Figure 1:
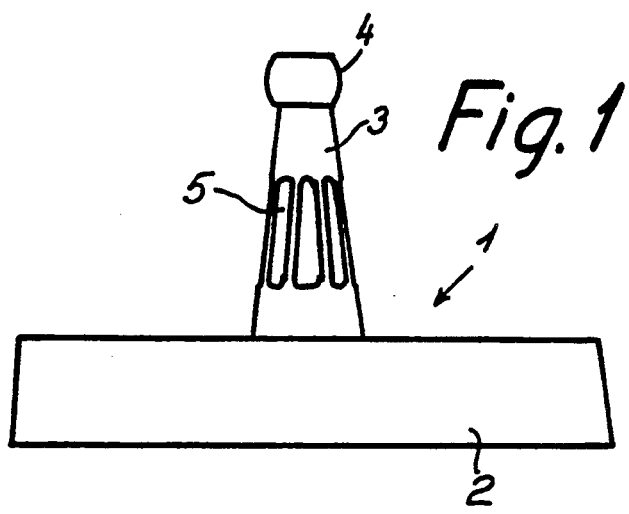

United States Patent

Mogensen

[11] Patent Number: 5,378,148
[45] Date of Patent: Jan. 3, 1995

[54] MODEL HOLDING MEANS AND ARTICULATOR FOR USE WITH DENTAL MODELS AND APPARATUS FOR ADJUSTMENT OF THE ARTICULATOR

[76] Inventor: Bent Mogensen, 22, 3tv Sokkelundsvej, DK-2400 Kobenhavn NV, Denmark

[21] Appl. No.: 982,742
[22] PCT Filed: Sep. 9, 1991
[86] PCT No.: PCT/DK91/00258
§ 371 Date: Mar. 17, 1993
§ 102(e) Date: Mar. 17, 1993
[87] PCT Pub. No.: WO92/03986
PCT Pub. Date: Mar. 19, 1992

[30] Foreign Application Priority Data
Sep. 10, 1990 [DK] Denmark ............... 2162/90

[51] Int. Cl.6 .................. A61C 11/00; A61C 19/00
[52] U.S. Cl. ........................ 433/64; 433/34; 433/55; 433/60
[58] Field of Search ............ 433/34, 55, 56, 57, 433/58, 60, 61, 64

[56] References Cited
U.S. PATENT DOCUMENTS

| | | | |
|---|---|---|---|
| 1,654,453 | 12/1927 | Brown | 433/58 |
| 1,798,518 | 3/1931 | Bennett | 433/55 |
| 2,621,407 | 12/1952 | Schlesinger | 433/57 |
| 4,103,424 | 8/1978 | Benjamin et al. | 433/58 |
| 4,548,581 | 10/1985 | Huffman | 433/64 |
| 5,007,829 | 4/1991 | Farrell | 433/57 |

Primary Examiner—Gene Mancene
Assistant Examiner—Nicholas D. Lucchesi
Attorney, Agent, or Firm—Kerkam, Stowell, Kondracki & Clarke

[57] ABSTRACT

Articulator for dental modelling, such as restoration of individual teeth and the manufacture of bridges or the like, comprising an upper part and a lower part mutually connected by a hinge, which makes it possible to simulate a movement approximately corresponding to a chewing movement, between the upper part and the lower part as well as a device for adjusting the upper part in relation to the lower part to establish a correct mutual engagement between the models mounted on the two parts and a subsequent fixation thereof. The articulator, of which the adjustment can take place shortly after the models have hardened and are ready for further working up, has an upper and lower part, each comprising a mould having walls with a toothing, one of the parts comprising a stanchion made of thermoplastics, the stanchion carrying one part of the hinge, with the hinge being separable. An apparatus having a nozzle is also provided, for supplying a jet of hot air through the stanchion, which is preferably tube shaped.

6 Claims, 2 Drawing Sheets

MODEL HOLDING MEANS AND ARTICULATOR FOR USE WITH DENTAL MODELS AND APPARATUS FOR ADJUSTMENT OF THE ARTICULATOR

BACKGROUND OF THE INVENTION

The present invention relates to a model holder and an articulator for dental modelling and comprises an upper part and a lower part mutually connected by means of a hinge, which makes it possible to simulate a movement approximately corresponding to a chewing movement, between the upper part and the lower part as well as means for adjusting the upper part in relation to the lower part in order to establish a correct mutual engagement between the models mounted on the two parts and a subsequent fixation thereof. Moreover, the invention relates to an apparatus for adjusting such an articulator.

From U.S. Pat. No. 4,548,581 an articulator for denture modelling is known, said articulator consisting of a hinged two part flexible element, each part ending in a ball-and-socket joint placed in a mounting element. The mounting elements are provided with a pin adapted to be glued in a groove in a cast model, which in the examples given is a complete jaw model or mould of either an upper jaw or a lower jaw. After the mounting of the mounting elements the two models or casts can be adjusted to correct engagement corresponding to the the bite registered from the patient, after which the two ball-and-socket joints are fixated by means of an adhesive. The articular can on account of the combination of the hinge and the two ball-and-socket joints be fully adequately adjusted, but is, due to the fact that during the mounting and the adjustment thereof two subsequent glueing operations are required, fairly slow to work with. For dental modelling consisting of the restoration of single teeth or smaller bridges and the like tasks. Where no cast of the whole set of teeth is available, the known apparatus is akward to handle, and the use of the known apparatus involves an unreasonably big consumption of time for fastening the models on a suitable stanchion, to which the connecting parts may be glued. This fastening normally takes place by means of pins to be inserted into bores in the model, and which pins are moulded in the stanchion, the number of pins being of such a size that a single tooth can be cut out of the model and mounted separately.

It is known in connection with the production of models to cast these in a rectangular mould with toothed walls. The model can be removed from the toothed mould and reinserted after having been divided or worked up in other ways, and on account of the-toothing also parts of the model can be put back in the mould in the same place, in which they were originally moulded. The mould can be cast in an articulator which may later be adjusted, but in all quite a number of operations with subsequent setting is required to produce an applicable model of a denture.

The object of the present invention is to provide an articulator, which is characteristic by means of the subject matter of the characterizing clause of claim 1.

Through mounting of the hinge of the articulator on a stanchion made of thermoplastics, which can be plastified through heating and fixated in a new position by cooling and by combining these features therewith that the models are directly cast in the upper and lower part of the articulator, a number of working processes will be superfluous in connection with the making of the model, said operations being admittedly per se not very time-consuming, but which per se requires a setting time of several minutes for the plaster or the adhesive used. Besides, the articulator is simple to make and suitable for being used only once. The hinge of the articulator should be separable to make it possible immediately to cast the model in the toothed mould, which is integral with the remaining part of the upper or lower part.

Preferred embodiments will appear from the dependent claims. It is in particular advantageous that the models cast in the moulds can be taken out and worked up, for instance cut through, and that it is possible to place the individual pieces correctly in the articulator again. For this purpose the moulds are provided with index rulers and with means for providing a corresponding impression in the cast model. The index of the ruler ensures a completely accurate re-placing.

The single ball-and-socket joint forming the hinge of the articulator cannot exactly imitate the chewing movement obtained by the anatomical jaw hinge, and such an imitation is not required. It is of great importance that a correct engagement between the upper and lower part of the denture can be established. From this position of engagement the required movement is very small and may be obtained from the elasticity of the stanchion and the other parts. Therefore, an exact definition of the placing of the hinge vis a vis the moulds is unimportant and the stanchion may be placed anywhere at the edge of the form part.

Figure 2:
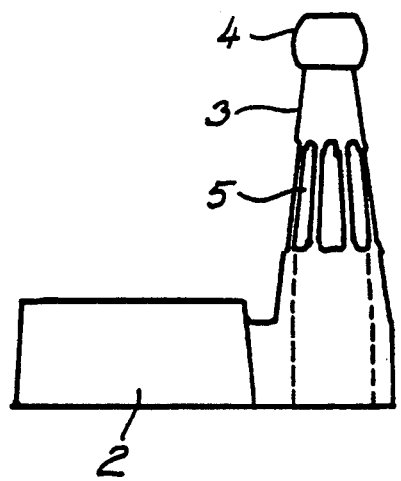
Figure 3:
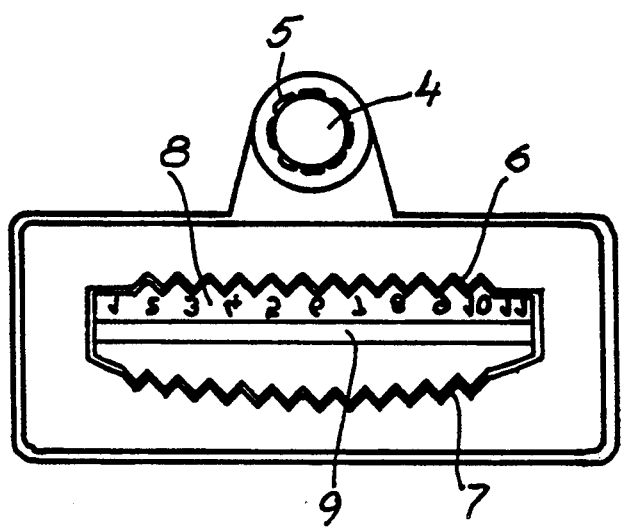
Figure 4:
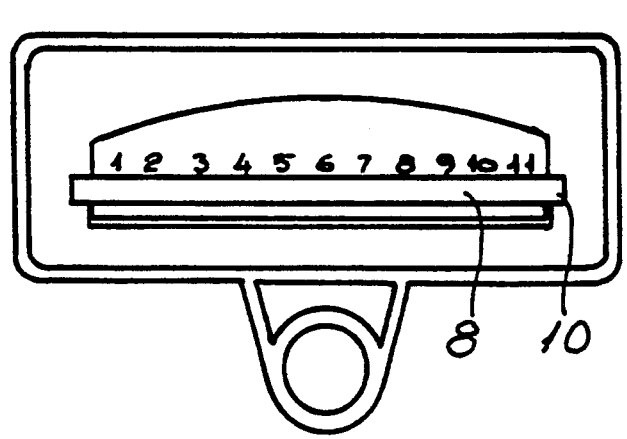
Figure 5:
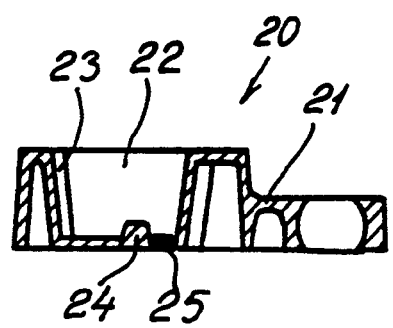
Figure 6:
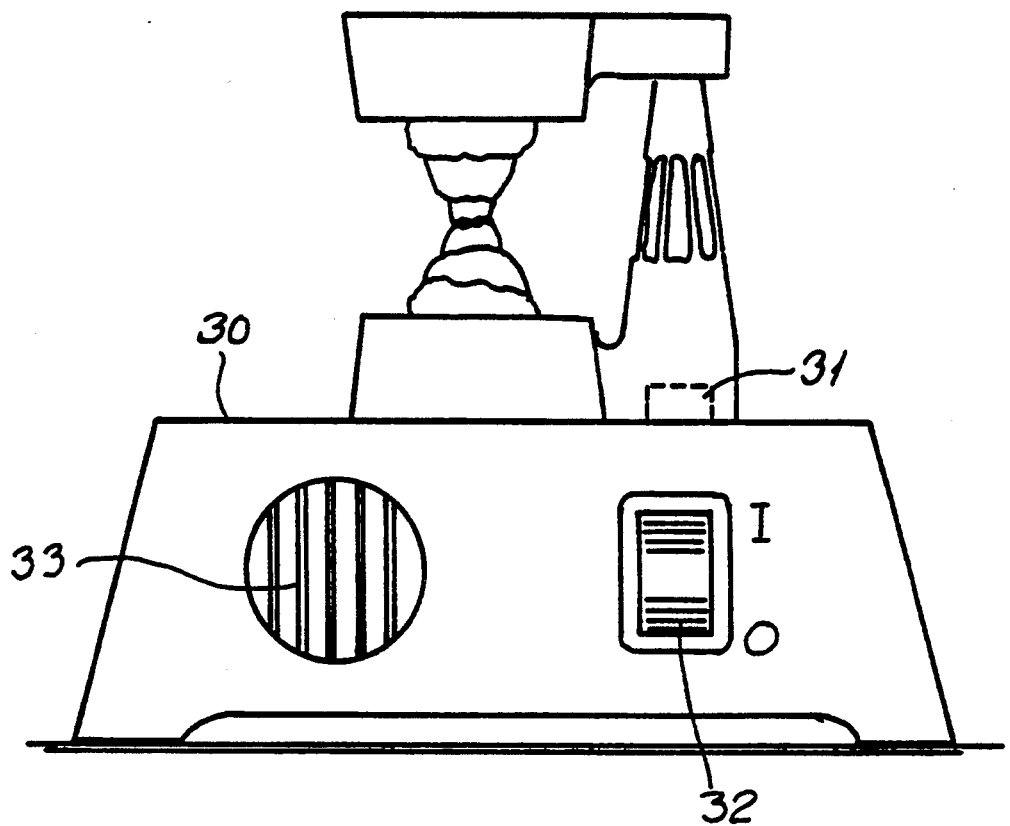

The invention will be described in detail in the following with reference to the drawing, in which FIG. 1 is an embodiment of a lower part of an articulator according to the invention seen from in front, FIG. 2 shows the lower part according to FIG. 1 from the side, FIG. 3 shows the under part according to FIG. 1 from above, FIG. 4 shows the under part according to FIG. 1 from below, FIG. 5 shows an upper part mating the lower part according to FIG. 1 in perspective through the hinge joint, and FIG. 6 is a lateral view of an adjustment apparatus for use in connection with the articulator according to claim 1.

The articulator according to the invention comprises a lower part and an upper part. An embodiment of a lower part 1 is shown in FIGS. 1, 2, 3, and 4. A sectional view of a mating upper part is shown in FIG. 5. The lower part 1 comprises a form part 2 and a stanchion 3, which is at the top provided with a hinge joint, preferably a ball-and-socket joint, the stanchion being provided with a ball-shaped bearing surface 4. The stanchion 3 is slightly conical and is hollows, a channel extending from the lower side of the stanchion and through it to a ring of openings 5. The part of the stanchion not being part of these openings, forms a grating which is fairly resistant to bending and twisting, so that the ball-and-socket joint 4 is fixated in relation to the form part 2. In FIG. 2 the lower part is seen from the side, and the cavity of the stanchion is indicated by dotted lines running form the bottom surface of the lower part to the openings 5.

The form part 2 of the lower part comprises a mould, in which a model of a bigger or smaller part of a denture can be cast in. The mould is best seen in FIG. 3, which shows the lower part 1 from above. In the embodiment shown the outline of the mould is oval and the mould has side walls 6, which partly have a considereably slip, so that the model made in the mould can be easily removed, and partly a toothing 7, which ensures that the model made in the mould or parts thereof can be replaced in the mould and be accurately fixated therein. To facilitate the accurate replacing of a model part in the mould, it may moreover be provided with a ruler 8 forming the bottom of the mould, and which is provided with an index making an impression in the model cast. The part of the bottom, which is provided with an index, may preferably be clipped in a small slot between a fixed ruler 9, which partly supports the form part and which partly at the under surface is provided with the same index as the clipped in ruler 8. The ruler 9 can in particular be seen in FIG. 4, which shows the lower part seen from below. The ruler 8 may be provided with a pair of finger grips 10, which make it easy to remove the ruler after the casting in of the model. Those parts of the form bottom, which cast in an index in the model, may possibly be surrounded by weakened or partly perforated areas, so that the part of the bottom, which provides the index impression in the model, can be pressed out, when the cast in model is set and removed from the mould. When inserting a part of the model, it has to be placed in such a way that the cast in index is placed opposite to the index visible on the outer surface of the mould.

In the embodiment shown in FIGS. 3 and 4 the cavity of the mould is elaborated in such a way that the cast in models can only be re-placed in one way. The possibility, when restoring single teeth, of erroneously placing the isolated tooth in relation to the teeth of the opposite jaw part is thereby eliminated. It may, however, be advantageous in certain cases to let the mould cavitiy with the toothed walls have the shape of two concentric spheres. It is thereby made possible to insert partition walls in the toothing, which may then at a later division of the model into single teeth serve as breaking instructions. The partition walls only have to be of such a height that the model is given sufficient strength to be handled, but should, however, weaken the model to such an extent that it can easily be broken in the desired place, perhaps after an incision on both sides of the tooth or the teeth to be isolated.

To the lower part 1 an upper part 20 corresponds, said upper part being provided with a form part 21 corresponding to the form part 2 shown in perspective in FIG. 5. Unlike the bottom part 1 the upper part is not provided with a stanchion, but solely a hinge joint 21, adapted to be clipped to the bearing surface after the casting of the model in the form cavity 22. The form part is in the same way as the form part 2 provided with toothed side walls 23 and a ruler 24 longitudinally to the bottom and a ruler 25 clipped in a slot in the bottom surface, said ruler being also provided with an index leaving an impression in the model.

The articulator according to the invention is used for dental modelling, for instance restoration of individual teeth or for bridge modelling. The model holder may possibly be used in an enlarged version in connection with denture work and makes a considerably simplified working process possible as compared to common practice. For use in denture work the cavity of the mould should be shaped like a horse-shoe like a normal set of teeth. On basis of the casts take of the mouth of a patient, models are made of the teeth or the set of teeth to be restored or perhaps replaced by a denture. The models are cast in the form parts 2 and 22, the form parts having not yet been connected in the hinged joint. After the setting or the plaster, by means of which the models have been cast in, the upper and lower part are connected, after which an adjustment has to be made so that an engagement between the models corresponding to the bite of the patient can be established. It is most practical that the models of the teeth in the upper and the lower jaw are cast in in the two moulds so that the necessary adjustment can be limited to a few millimeters only, which facilitates the adjustment, but which is no prerequisite for making it. Adjustment is carried out thereby that the stanchion, which is made from thermoplastics, is heated to such a temperature that it plastifies. While the thermoplastics is plastified, the upper and lower part are adjusted with respect to one another, and when the desired engagement is established, the stanchion is allowed to cool, after which the thermoplastics hardens again, the adjustment thus becoming permanent. In the embodiment shown in the drawing, in which the stanchion is tubular and bears a ring of openings, the plastic condition is very quickly reached at the ribs between the openings, and these ribs form a grating, which in plastified condition is deformable by use of very little force, and which after being hardened again, acquire a comparatively big resistance towards bending and twisting. In plastified condition the ribs may be both stretched and compressed, so that the adjustment can take place not only horizontally, but also vertically. If the openings are elongate, so that the ribs between them acquire a length of 10–15 mm, it is possible to make adjustments of several millimeters between the two parts.

After the adjustment the models can be removed from the moulds and used in the subsequent denture work. In this connection it is possible to cut the models in several pieces and replace them in the form parts, where on account of the toothing it will be possible to fixate them in their original place. To facilitate the positioning, the model may be provided with an impression from the ruler 8, and it will then be possible to place index opposite to the same figure on the ruler 9.

Even though, for adjustment reasons, it is necessary to make only the stanchion from thermoplastics, it is preferred to produce both the upper part as well as the lower part of plastics material cast integrally from thermoplastics by means of die casting, These plastic parts may be made from any plastics material suitable for die casting. When producing the parts of plastics it is preferable to discard them after use, the stanchion becoming after several adjustments somewhat weakened.

The upper and lower parts shown in the drawing are in particular suited for dentures, where only one model of a half jaw is used. Through a suitable shaping of the form parts they might also be applicable for the making of complete dentures. It will for instance be possible to make the form part approximately horse-shoe shaped, making it possible to cast in a model of a whole jaw.

For use in the adjustment it is advantageous to use the apparatus shown in FIG. 6, said apparatus comprising a support surface 30 for the lower part of the articulator and an upwards directed nozzle, through which, by activation of a control button 32, a jet of hot air can be given off, said hot air having a temperature, which just soften the plastics adequately. It is preferable that the apparatus, when the control button is disconnected, gives off for some time an air jet of ambient temperature so that the plastics of the stanchion, when the adjustment is terminated, cools quickly, so that there is no danger in touching the articulator during the subsequent denture work. The apparatus contains an electric fan with an air intake 33. In the connecting channel from the fan to the nozzle a preferably thermostatically controlled heating element is mounted.

I claim:

1. Articulator for dental modelling, such as restoration of single teeth and the manufacture of bridges or the like, and comprising an upper part (20) and a lower part (1) mutually connected by a hinge (4), which makes it possible to simulate a movement approximately corresponding to a chewing movement, between the upper part (20) and the lower part (1) as well as means for adjusting the upper part in relation to the lower part in order to establish a correct mutual engagement between models mounted on the two parts and a subsequent fixation thereof, wherein the lower part (1) comprises a form part (2), on the upper surface of which a mould is arranged, said form part having side faces and a stanchion (3) upstanding at one of the side faces of the form part (2), which stanchion is made from thermoplastics and carries one part of the hinge (4); said stanchion (3) being provided with a cavity extending from an inlet in the bottom surface of the lower part to a plurality openings (5) positioned approximately at half of the height of the stanchion; said upper part (20) comprising a form part (21), having a lower surface, said lower surface comprising a second mould (22), the internal walls (6) of said moulds having a toothing (7); and wherein said hinge is a ball-and-socket joint (4).

2. Articulator according to claim 1, wherein the form part (1), on which the stanchion (3) is mounted, is cast integrally from thermoplastics.

3. Articulator according to claim 1 wherein the mould of the form part is elongate.

4. Articulator according to claim 3, wherein the mould is provided with a removable bottom with an index ruler (8) adapted to provide an impression in the cast model as well as a stationary ruler (9) or surface with a corresponding index, which is visible from the outside of the mould of the form part and parallel to the index ruler or surface.

5. Articulator according to claim 1, wherein the openings (5) have such a shape and extension that the stanchion (3) forms a grating, which is resistant to bending and twisting.

6. Articulator according to claim 1, wherein the mould of the form part is elongate and curved.

* * * * *

UNITED STATES PATENT AND TRADEMARK OFFICE
CERTIFICATE OF CORRECTION

PATENT NO. : 5,378,148
DATED : January 3, 1995
INVENTOR(S) : Bent MOGENSEN

It is certified that error appears in the above-indentified patent and that said Letters Patent is hereby corrected as shown below:

In column 5, line 26 [claim 1, line 18]: after "plurality" insert -- of --.

In column 6, line 14 [claim 4, line 2]: after "mould" insert -- of the form part --.

Signed and Sealed this

Twenty-first Day of March, 1995

Attest:

BRUCE LEHMAN

Attesting Officer        Commissioner of Patents and Trademarks